US011905257B2

(12) United States Patent
Fretta et al.

(10) Patent No.: US 11,905,257 B2
(45) Date of Patent: Feb. 20, 2024

(54) MANUFACTURING PROCESS FOR PREPARING GADOTERIDOL

(71) Applicant: BRACCO IMAGING S.P.A., Milan (IT)

(72) Inventors: Roberta Fretta, Collegno (IT); Luciano Lattuada, Cassina de'Pecchi (IT); Gabriele Meli, Udine (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

(21) Appl. No.: 18/039,540

(22) PCT Filed: Dec. 1, 2021

(86) PCT No.: PCT/EP2021/083715
§ 371 (c)(1),
(2) Date: May 31, 2023

(87) PCT Pub. No.: WO2022/117619
PCT Pub. Date: Jun. 9, 2022

(65) Prior Publication Data
US 2023/0391735 A1 Dec. 7, 2023

(30) Foreign Application Priority Data
Dec. 4, 2020 (EP) ..................................... 20211919

(51) Int. Cl.
*C07D 257/02* (2006.01)
(52) U.S. Cl.
CPC ................................. *C07D 257/02* (2013.01)
(58) Field of Classification Search
CPC .................................................. C07D 257/02
See application file for complete search history.

(56) References Cited

U.S. PATENT DOCUMENTS

| | | | |
|---|---|---|---|
| 4,371,704 A | 2/1983 | McEntire et al. | |
| 10,407,412 B2* | 9/2019 | Boi | C07D 257/02 |
| 10,793,533 B2* | 10/2020 | Boi | C07D 403/12 |
| 11,007,283 B2* | 5/2021 | Lattuada | A61K 49/106 |
| 2020/0397924 A1* | 12/2020 | Zhang | A61K 49/106 |
| 2021/0380542 A1* | 12/2021 | Pullagurla | C07F 5/003 |

FOREIGN PATENT DOCUMENTS

| | | |
|---|---|---|
| CN | 110078685 A | 8/2019 |
| CN | 110835326 A | 2/2020 |
| EP | 0988294 B1 | 11/2005 |

OTHER PUBLICATIONS

Dischino, Inorg Chem, 1991, vol. 30, 1265-1269. (Year: 1991).*
Bayardon, J., et al., "Propylene Carbonate as a Solvent for Asymmetric Hydrogenations," Angew Chem. Int. Ed., 46:5971-5974 (2007).
Bottrill, M. et al., "Lanthanides in magnetic resonance imaging," Chem. Soc. Rev., 35:557-571 (2006).
Busch, J., et al., "Final Report on the Safety Assessment of Propylene Carbonate," Journal of the American College of Toxicology, 6:23-51 (1987).
Holger, B., et al., "Propylene oxide," In: Ullmann's Encyclopedia of Industrial Chemistry, Wiley-VCH Verlag GmbH & Co. KGaA, Weinheim, Germany (2012).
International Search Report and Written Opinion for PCT/EP2021/083715, dated Mar. 7, 2022.
Runge, M., et al., "The Developmental History of the Gadolinium Chelates as Intravenous Contrast Media for Magnetic Resonance." Invest. Radiol., 46:807-816 (2011).
Schaffner, B., et al., "Organic Carbonates as Solvents in Synthesis and Catalysis," Chem. Rev., 110:4554-4581 (2010).

* cited by examiner

*Primary Examiner* — D Margaret M Seaman
(74) *Attorney, Agent, or Firm* — VIVICAR Law, PLLC

(57) ABSTRACT

The invention relates to a process for preparing Gadoteridol of formula (I). In particular, the process comprises the use of propylene oxide in the alkylation step of the compound of formula (II), wherein propylene oxide is directly reacted with the compound of formula (II) without being isolated, and wherein propylene oxide is obtained on demand by decomposition of propylene carbonate in the presence of an alkaline or alkaline earth metal halide as catalyst.

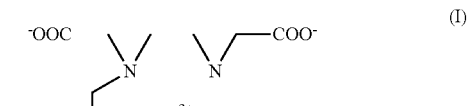

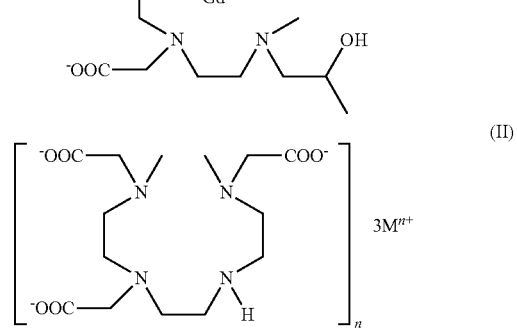

11 Claims, 1 Drawing Sheet

MANUFACTURING PROCESS FOR PREPARING GADOTERIDOL

CROSS-REFERENCE TO RELATED APPLICATIONS

This application is the national stage application of corresponding international application number PCT/EP2021/083715, filed Dec. 1, 2021, which claims priority to and the benefit of European application no. 20211919.4, filed Dec. 4, 2020, which is hereby incorporated by reference in its entirety.

BACKGROUND OF THE INVENTION

The invention is in the field of Magnetic Resonance Imaging (MRI) contrast agents and, in particular, deals with a new synthetic process for manufacturing Gadoteridol, a macrocyclic gadolinium chelate, which is the active pharmaceutical ingredient (API) of Prohance (M. Bottrill, L. Kwok, N. J. Long, Chem. Soc. Rev. 2006, 35, 557-571).

Gadoteridol was the first non-ionic macrocyclic gadolinium chelate to be developed for clinical use and has been on the market for about 30 years (V. M. Runge, T. Ai, D. Hao, X. Hu, Invest. Radiol. 2011, 46, 807-816).

A process for preparing Gadoteridol is disclosed in EP 0 988 294. The disclosed process is summarized in the following Scheme 1:

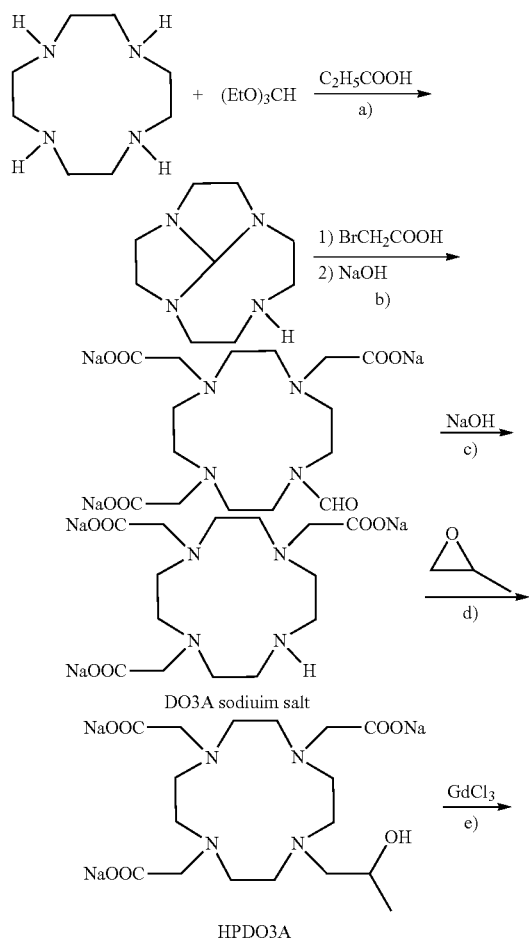

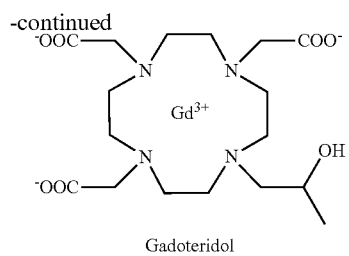

Gadoteridol

As illustrated in Scheme 1, 1,4,7,10-tetraazacyclododecane is reacted with triethyl orthoformate, in the presence of an acid to obtain 5H,9bH-2a,4a,7,9a-octahydro-tetraazacycloocta[cd]pentalene (step a);

the obtained 5H,9bH-2a,4a,7,9a-octahydro-tetraazacycloocta[cd]pentalene is reacted with bromoacetic acid and NaOH to give the sodium salt of 10-formyl-1,4,7,10-tetraazacyclododecane-1,4,7-triacetic (step b) which is hydrolyzed in step c), without being isolated, to give 1,4,7,10-tetraazacyclododecane-1,4,7-triacetic acid sodium salt (DO3A);

1,4,7,10-tetraazacyclododecane-1,4,7-triacetic acid sodium salt (DO3A) is alkylated in step d) with propylene oxide to give 10-(2-hydroxypropyl)-1,4,7,10-tetraazacyclododecane-1,4,7-tri-acetic acid as sodium salt (HPDO3A), which is complexed with gadolinium chloride in step e), without being isolated to give Gadoteridol, that is then purified and crystallized to obtain the final API.

The alkylation step d) is carried out using commercial propylene oxide (PO), which is a liquid with a low boiling point (34° C.), extremely flammable and classified as a toxic reagent according to the current GHS regulations (H350 and H340). As clearly stated in any material safety data sheet (MSDS) (see for instance the MSDS by Merck; see also D. Kahlich, U. Wiechern, J. Lindner, "Propylene oxide" in Ullmann's Encyclopedia of Industrial Chemistry, Viley-VCH Verlag GmbH & Co. KGaA, Weinheim, 2005), propylene oxide may cause cancer, genetic defects, skin and eye irritation and respiratory irritation.

For all these reasons propylene oxide must be handled and stored with extreme attention and care. In order to overcome these problems, a deep investigation was carried out in order to evaluate possible less toxic alternatives to this compound.

It has now been found that propylene carbonate (PC) can be used as precursor of PO in a process for preparing Gadoteridol, comprising the conversion of PC to PO, that is not isolated and collected, but immediately used in the next alkylation step, maintaining the high yields and the impurity profile of Gadoteridol as obtained by the known industrial process.

PC is a safe reagent from a toxicological point of view and its use in the manufacturing process for preparing Gadoteridol allows to avoid issues related to transportation, storage and handling of a toxic reactive such as PO; moreover, the cost is comparable to PO.

A number of publications describe the use of cyclic carbonates to prepare a variety of functionalized alcohols and epoxides. In particular, U.S. Pat. No. 4,371,704 discloses the conversion of substituted ethylene carbonates to substituted epoxides by heating the cyclic carbonates using different alkaline metal halides as catalysts. In particular, U.S. Pat. No. 4,371,704 discloses the conversion of PC to PO by heating PC in the presence of a catalyst selected from lithium fluoride, sodium fluoride, potassium fluoride, sodium chloride and potassium chloride. The document reports that PO is produced with a very low selectivity and yield when LiI is used as catalyst. KI, instead, gives good selectivity and yield but in a relatively long time, namely 4.8 h. NaI is not mentioned among the catalysts useful to give propylene oxide. Thus, the document concludes that LiI is the less selective iodide for propylene oxide production from propylene carbonate.

SUMMARY

The present invention relates to the synthesis of Gadoteridol in which propylene oxide is generated when needed by thermal degradation of propylene carbonate, catalyzed by alkaline metal halides (Scheme 2).

SCHEME 2

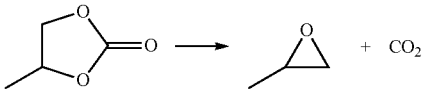

The generated propylene oxide is not stored but immediately employed in the synthesis of gadoteridol. This procedure is called "on site" or "on demand".

In this way all the issues and problems related to transportation, storage and handling of propylene oxide are avoided.

On the other hand, propylene carbonate has significant benefits since it is considered as a safe and eco-friendly compound due to its high boiling point (240° C.), low vapor pressure, biodegradability and low toxicity (J. Bayardon, J. Holz, B. Schaffner, V. Andrushko, S. Verevkin, A. Preetz, A. Borner, Angew. Chem. Int. Ed. 2007, 46, 5971-5974; J. Am. College Toxicol. 1987, 6, 23-51). Moreover, propylene carbonate is largely employed as solvent since it is available on an industrial scale at relatively low costs and can be stored safely in large amounts (B. Schaffner, F. Schaffner, S. P. Verevkin, A. Borner, Chem. Rev. 2010, 110, 4554-4581).

DESCRIPTION OF THE INVENTION

Figure 1:
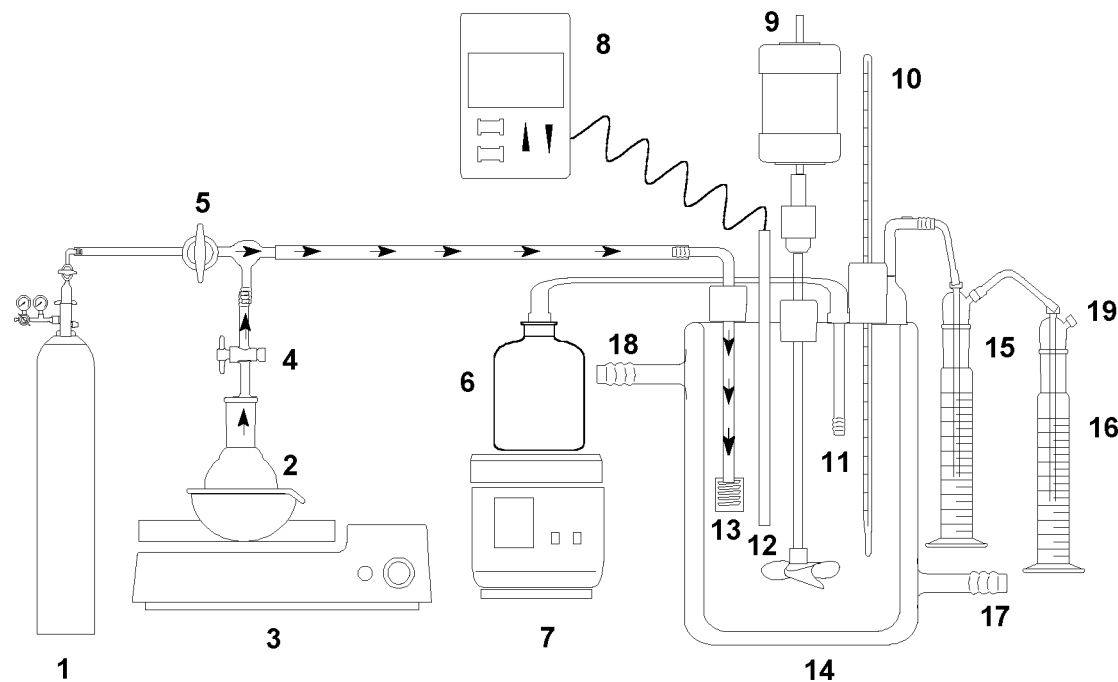
FIG. 1 shows a schematic representation of an apparatus which can be used in the process of the invention for generating PO and using it directly in the alkylation step i).

Object of the present invention is a process for preparing Gadoteridol of formula (I):

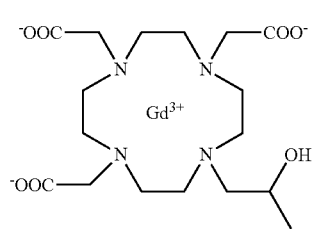

comprising the following steps:
i) reacting propylene oxide of formula:

with the compound of formula (II):

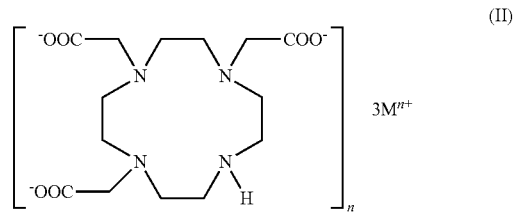

wherein M is an alkaline or alkaline earth metal, preferably an alkaline metal, most preferably Na, and n is 1 or 2;
to obtain the compound of formula (III):

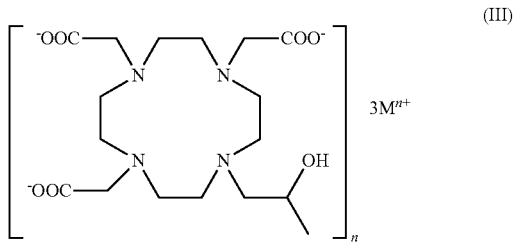

wherein M and n are as defined above;
ii) complexing the obtained compound of formula (III) with $Gd^{3+}$ metal ion to obtain Gadoteridol of formula (I) characterized in that:
propylene oxide is prepared by decomposition of propylene carbonate of formula:

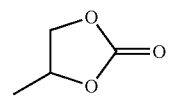

in the presence of a metal halide as catalyst and directly reacted with the compound of formula (II) without being isolated.

More particularly, the decomposition of propylene carbonate is carried out by heating propylene carbonate in the presence of a catalyst which is an alkaline or alkaline earth metal halide.

PO is immediately reacted with the compound of formula (II) as soon as it is obtained by the decomposition of PC without isolation and/or collection.

PO is obtained by heating PC according to the thermal decomposition reaction reported in the above Scheme 2. PC is a liquid at the reaction temperature. The decomposition product, i.e. PO, is a low boiling product, which is in gaseous form at the reaction temperature and can be directly conveyed and bubbled into a solution of the compound of formula (II) as soon as it is produced by the decomposition reaction, without isolation and/or collection.

In addition to the gaseous propylene oxide, the decomposition of the PC produces carbon dioxide which is transferred into the solution of the compound of formula (II) together with the PO.

Preferably the alkaline or alkaline earth metal halides used as catalyst in the preparation of propylene oxide are selected from sodium, potassium, lithium, magnesium or calcium iodide, bromide, chloride or fluoride. More preferably the metal halides are selected from sodium, potassium or lithium bromide or iodide, iodides being most preferred.

Particularly preferred catalysts are sodium and lithium iodides, most preferred being sodium iodide.

The amount of the catalyst used in the decomposition of propylene carbonate may range from 0.1% w/w to 100% w/w of the amount of propylene carbonate, more preferably from 0.1% w/w to 5.0% w/w and most preferably from 0.1% w/w to 2.0% w/w, e.g. 0.5% w/w.

The decomposition of PC is preferably carried out by heating at a temperature ranging from 160° C. to 250° C., most preferably from 180° C. to 220° C., e.g. 200 ° C.

In the alkylation step i) the compound of formula (II) is preferably dissolved in water.

The alkylation is carried out according to the conditions disclosed in EP0988294 and in the cited references. In particular, the alkylation reaction is conveniently performed at a temperature ranging from 20° C. to 50° C. During alkylation the pH is maintained at a basic value, preferably above 11.0, by addition of a base such as KOH or NaOH, more preferably NaOH.

The complexation step ii) is carried out according to known procedures, for instance by stoichiometric addition of a suitable Gd (III) derivative, particularly an oxide such as $Gd_2O_3$ or, preferably, a gadolinium salt such as $GdCl_3$, to the solution obtained in step i). In one embodiment, the complexation reaction of step ii) is carried by adding a gadolinium salt, e.g. $GdCl_3$ in water into the solution of the ligand obtained in step i) of the process and adjusting the pH in a range from 6.5 to 7.5. The solution is maintained at a temperature ranging from 25° C. to 60° C. for a time ranging from 0.5 to 1.5 hours until the complexation is complete.

Before the complexation step ii), the solution obtained in step i) can be added with an acid, preferably HCl, to neutralize $Na_2CO_3$, that is thus eliminated as $CO_2$.

In one embodiment, the solution of HPDO3A obtained in step i) is cooled at a temperature of about 25° C. and then added with HCl up to a final pH of about 4.5, causing $CO_2$ formation and bubbling. Then the gadolinium salt is loaded, and the complexation is performed according to known procedures (see e.g. EP 0 988 294).

In one alternative embodiment, the solution of HPDO3A obtained in step i) is loaded with the gadolinium salt and the pH is then adjusted to 4.0-5.0 by adding HCl to neutralize $Na_2CO_3$, and the complexation is performed according to known procedures, (see, e.g. the above cited reference).

This alternative implementation, which comprises a change in the order of addition of the Gadolinium salt and HCl allows an advantageous reduction of the amount of HCl necessary to achieve the desired pH conditions, enabling the neutralization of the $Na_2CO_3$.

The compound of formula (II) can be obtained as summarized in the above Scheme 1 or as reported in EP 0 988 294, which describes the preparation of Gadoteridol starting from 1,4,7,10-tetraazacyclododecane without isolating any of the intermediate products.

In a preferred embodiment, the alkylation reaction of step i) is carried out using a compound of formula (II) coming from the previous preparation steps without isolation.

Propylene oxide is prepared in a first reactor (decomposition reactor, usually a flask when working on a small scale), by heating propylene carbonate in the presence of an alkaline or an alkaline earth metal halide and the forming propylene oxide is directly fed to another reactor (alkylation reactor, usually a jacketed reactor), containing compound (II).

The necessary amount of propylene carbonate is added in the decomposition reactor and heated in the presence of an alkaline or alkaline earth metal halide.

The conversion from propylene carbonate to propylene oxide can be carried out in a batch mode (e.g. by adding propylene carbonate in one portion in the decomposition reactor) or alternatively in a semi-batch or continuous mode, i.e. propylene carbonate can be fed continuously, or in portions in the decomposition reactor.

Figure 2:
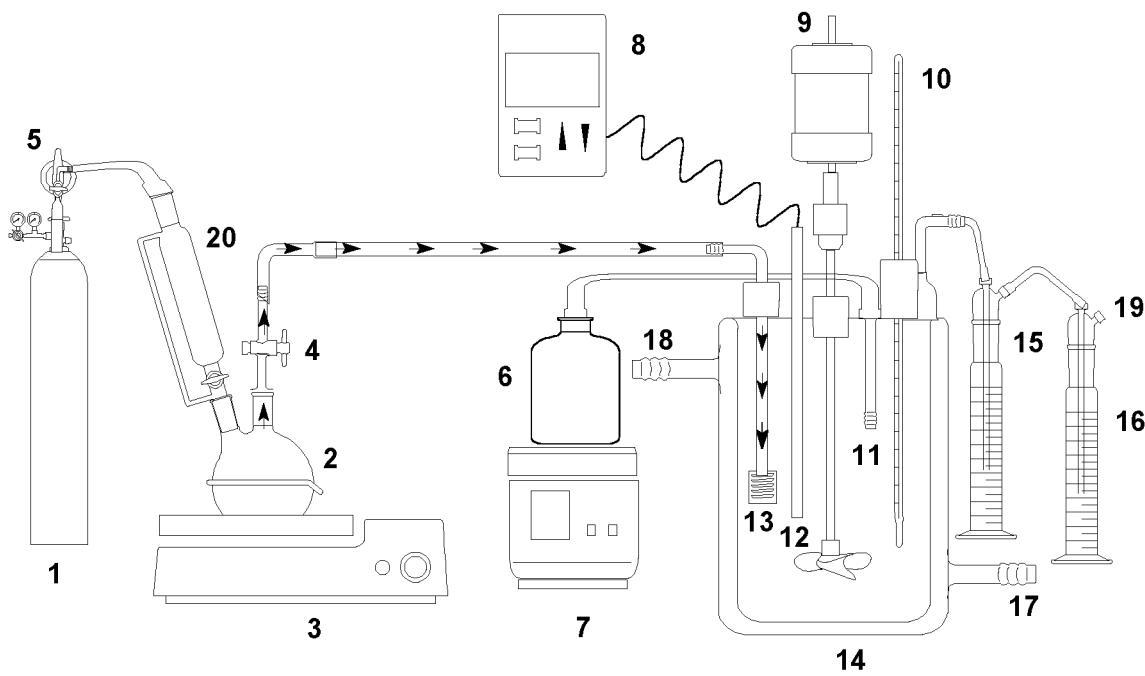
FIG. 2 shows a schematic representation of an alternative apparatus wherein PC is added continuously or in portions to refill the flask wherein PO is generated.

FIG. 1 or FIG. 2 illustrate two different exemplary apparatus which can be used for the preparation of propylene oxide and the alkylation step (i) according to the invention.

In FIG. 1 and FIG. 2 (1) is a nitrogen cylinder, (2) is a flask, (3) is a heating system, (4) and (5) are valves, (6) is a container for NaOH, (7) is a pumping system (e.g. Dosimat), (8) is a pH meter, (9) is a mechanical stirrer, (10) is a thermometer, (11) is a dripper for NaOH, (12) is pH meter probe, (13) is a porous glass tip, (14) is a jacketed reactor, (15) is a trap filled with 50% sulfuric acid, (16) is a trap filled with 30% sodium hydroxide, (17) is an inlet for heating/refrigerating fluid, (18) is an outlet for heating/refrigerating fluid, (19) is a vent and (20) is a dropping funnel.

While the equipments illustrated in the FIGS. 1 and 2 are generally presented at a laboratory scale, they can be easily scaled-up to an industrial scale by the skilled person.

Using the apparatus of FIG. 1, all the required amounts of propylene carbonate and catalyst are loaded in the flask (2). The temperature is increased to a temperature from 160° C. to 250 ° C. and kept for a time ranging from 0.5 to 2 h depending on the temperature, on the catalyst amount and on the type of catalyst. For example, when working at 200° C., 1 h is sufficient to obtain the complete decomposition of propylene carbonate, or even less, e.g. about 0.5 h when using NaI or LiI as catalysts. During this time the generated propylene oxide and $CO_2$ are transported by a nitrogen stream and bubbled directly into the jacketed reactor (14), through a pipe connected with a terminal porous glass tip (13) (this allows to obtain small gas bubbles that were easily dissolved, assuring the complete propylene oxide and $CO_2$ solubilization in the reaction mixture). In this way, in the reactor (14), propylene oxide can react with the compound of formula (II) to give the compound of formula (III) while 30% NaOH is continuously added, for instance by using a dosing system, e.g. a Dosimat apparatus, to keep the pH of the alkylation reaction at a basic value.

Alternatively, the apparatus of FIG. 2 can be used. An amount of propylene carbonate (e.g. about ⅓ of the total) and the proper amount of the catalyst determined over the weight of the starting portion of the PC, are loaded in the flask (2). The temperature is increased to a temperature from 160° C. to 250° C., for example 200 ° C., and kept for a time ranging from 0.5 to 9 hours, depending on the equipment used, the temperature, and the amount of catalyst, preferably from 0.5-3 hours, to obtain the decomposition of propylene carbonate. The generated propylene oxide and $CO_2$ are conveyed by a nitrogen stream and bubbled directly into the jacketed reactor (14), through a pipe connected with a terminal porous glass tip (13). During the time of the reaction additional propylene carbonate is continuously added through a dropping funnel to the flask 2, reintegrating the converted amount of PC and keeping a constant level in flask (2). Interestingly, no further catalyst is instead added.

In this way, the flow of propylene oxide arriving in the reactor (14) can immediately react with the compound of formula (II) to give the intermediate of formula (III) while 30% NaOH is continuously added, e.g. with a Dosimat apparatus, to keep the pH of the reaction constant at a basic value, as above said.

An advantage of using the proposed method, e.g. the semi-batch or continuous mode using the equipment schematized in FIG. 2, is the reduction of the amount of catalyst used, which is actually calculated only on the portion of PC initially loaded in the reactor, and no further addition is necessary during the refilling of propylene carbonate. Moreover, this set up is particularly advantageous when operating on a large scale: in fact, the exploitation of a continuous feeding of the PC to the system allows the use of a small size decomposition reactor which is more easily heated, thus reducing the energy consumption needed to reach the high temperature requested by the conversion reaction.

The present process allows avoiding not only the storage of a toxic and flammable substance such as PO but also its accumulation in the production plant since the PO produced by the decomposition reacts immediately in the alkylation reaction.

Experimental Part

Procedures

The concentration of 1,4,7,10-tetraazacyclododecane-1,4,7-triacetic acid sodium salt (compound (II), DO3A) in the starting solution was determined by complexometric titration and the alkylation to 10-(2-hydroxypropyl)-1,4,7,10-tetraazacyclododecane-1,4,7-tri-acetic) acid sodium salt (compound (III), HPDO3A) was monitored by HPLC analysis.

The impurity profile of 10-(2-hydroxypropyl)-1,4,7,10-tetraazacyclododecane-1,4,7-tri-acetic) acid sodium salt (compound (III)) and Gadoteridol solutions were evaluated by using HPLC analysis.

Catalyst Screening

The screening of the PC decomposition catalysts was performed by keeping fixed the decomposition temperature at 200° C., and the PC amount of 2.0 equivalents (calculated versus DO3A amount) and varying the type and the amount of the catalyst, determined as % (w/w) over the starting PC. The alkylation reactions were then carried out under same operative conditions (e.g. including same pH and temperature) for 5 h. NaOH was used to neutralize $CO_2$ generated from the PC decomposition.

Details are provided in the following representative example using NaI as conversion catalyst.

EXAMPLE 1

Preparation of 10-(2-hydroxypropyl)-1,4,7,10-tetraazacyclododecane-1,4,7-tri-acetic acid sodium salt (Compound (III)) by Conversion of propylene carbonate to propylene oxide in the Presence of NaI and Direct Alkylation of 1,4,7,10-tetraazacyclododecane-1,4,7-triacetic acid sodium salt (DO3A sodium salt, Compound (II))

The reaction was carried out using the equipment described in FIG. 1.

A solution of 1,4,7,10-tetraazacyclododecane-1,4,7-triacetic acid sodium salt (400 g; 0.24 mmol/g) was loaded in a 1 L reactor (reactor 14) and the pH was adjusted with 37% HCl (24.4 g) between 11.5±12.5 at 25° C. The temperature was increased to 40-45° C. and kept during the following Propylene Oxide and $CO_2$ addition.

A portion of propylene carbonate (19.1 g) and NaI (0.096 g) were loaded in a 50 mL flask (2). The temperature was increased to 200° C. promoting the decomposition of PC generating PO and $CO_2$, that were bubbled directly into reactor 14, through a pipe connected with a terminal porous glass tip.

The flask temperature was kept at 200° C. for 1 h, sufficient to achieve the complete degradation of the PC.

In reactor 14 the pH was maintained at the above value during PO and $CO_2$ bubbling, dosing automatically 30% NaOH (49.9 g).

The alkylation reaction was kept at 40-45° C. for a total of 5 hours, checking the end of the reaction by HPLC analysis. The temperature of the alkylation medium was then decreased to 25° C.

The test was repeated by changing alkaline iodides (used as PC decomposition catalyst), and thereof amounts, and keeping the decomposition temperature and PC: compound (II) ratio used in the previous example test fixed. The obtained results are summarized in TABLE 1.

TABLE 1

| Catalysts | | PC conversion | | Residual compound (II) at the end of the alkylation |
|---|---|---|---|---|
| Type | %[1] w/w | % mol/mol | Time[2] (h) | % (w/w) | % (HPLC area) |
| KI | 1.00 | 0.62 | 3.0 | 99.0 | 0.2 |
| NaI | 1.00 | 0.68 | 0.5 | 99.0 | 0.1 |
| LiI | 1.00 | 0.76 | 0.5 | 99.0 | 0.4 |
| KI | 0.50 | 0.31 | 2.5 | 94.5 | 2.0 |
| NaI | 0.50 | 0.34 | 1.0 | 99.0 | 0.4 |
| LiI | 0.50 | 0.38 | 1.0 | 99.0 | 0.3 |

[1]% calculated versus the starting PC.
[2]Time at which the reaction stops, detected by the end of the $CO_2$ bubbling and/or pH stabilization.

In the above table, the % conversion of the PC (w/w over starting PC) was determined by weighing the reactor.

The obtained results show that, unexpectedly, the use of the selected iodide catalysts and, especially, NaI and LiI, allows to significantly reduce both the required amount of catalyst and the time necessary to achieve the complete conversion of PC into PO.

EXAMPLE 2

Preparation of 10-(2-hydroxypropyl)-(1,4,7,10-tetraazacyclododecane-1,4,7-tri-acetic) acid sodium salt (HPDO3A, Compound (III)) by PC Conversion to PO and Alkylation of 1,4,7,10-tetraazacyclododecane-1,4,7-triacetic acid sodium salt (DO3A sodium salt, Compound (II))

The reaction was carried out using the equipment described in FIG. 2.

A solution of 1,4,7,10-tetraazacyclododecane-1,4,7-triacetic acid sodium salt (7.519 kg; 0.266 mol/kg corresponding to 2.00 mol) was loaded in an 8 L reactor (reactor 14) and the pH was adjusted with 37% HCl (497 g) between 11.5÷12.5 at 25° C. The temperature was increased to 40-45 °C. and kept during the following PO and CO$_2$ addition.

A first portion of PC (100 g) and NaI (1.0 g) were loaded in a 100 mL flask (2). The temperature was increased to 200° C. and the decomposition of PC generated PO and CO$_2$, that were bubbled directly into reactor 14, through a PVC pipe connected with a terminal porous glass tip (this allowed to obtain small gas bubbles that assured the complete PO and CO$_2$ solubilization in the reaction mixture).

The flask temperature was kept at 200° C. for 9 h and, during this time, an additional amount of PC (252 g), sufficient to achieve the completion of the reaction, was refilled through a dropping funnel (20), reintegrating the converted amount and keeping a constant level of PC in flask (2). No further NaI amount is added during the PC refill.

In reactor 14 the pH was maintained in the range 11.5÷12.5 during PO and CO$_2$ bubbling, dosing automatically 30% NaOH (919.2 g).

The alkylation was monitored every hour by HPLC analysis and was completed after the decomposition of 1.72 equivalents of PC.

EXAMPLE 3

Preparation of Gadoteridol (Compound of Formula (I)) by Complexation of 10-(2-hydroxypropyl)-1,4,7,10-tetraazacyclododecane-1,4,7-tri-acetic acid sodium salt (Compound (III), HPDO3A sodium salt) with GdCl$_3$ Preparation of GdCl$_3$ Water (500 g) and Gd$_2$O$_3$ (362.5 g) were loaded in a 2 L flask; 37% HCl (656.3 g) was dropped in 1 h at 25÷30° C. The suspension was heated to 90÷95° C., maintained under stirring until complete dissolution and then cooled to 25° C.

Complexation of 10-(2-hydroxypropyl)-1,4,7,10-tetraazacyclododecane-1,4,7-tri-acetic) acid sodium salt (Compound (III), HPDO3A)

The solution of HPDO3A (compound (III) containing theoretical 2.00 mol of HPDO3A) was transferred in to a 10 L reactor, then a first portion of 37% HCl (400 g) was slowly loaded in 5 h, maintaining the temperature below 30° C., to neutralize completely the Na$_2$CO$_3$, causing CO$_2$ formation and bubbling (final pH=4.5).

The GdCl$_3$ solution was slowly loaded over 1 hour; a second portion of 37% HCl (291 g) was loaded and the solution was kept under stirring for 2 h (pH about 1.7).

The temperature was increased to 50° C., the pH was corrected to 7.0÷7.5 using 30% NaOH (1.17 kg; 8.78 mol) and the complexation was completed in 2 h.

The results of the alkylation, carried out according to the process of the invention described above are reported in TABLE 2 and compared to a standard alkylation with commercial PO (disclosed in EP 0 988 294). The impurity profile of 10-(2-hydroxypropyl)-1,4,7,10-tetraazacyclododecane-1,4,7-tri-acetic acid sodium salt (compound (III)) obtained by the process of the invention is comparable to that obtained by using commercial PO and no new impurities are observed.

TABLE 2

| Propylene oxide | (% HPLC area) | | | |
|---|---|---|---|---|
| Source | eq. vs compound (II) | Compound (II) | Compound (III) | Other impurities (total) |
| Commercial | 1.90 | N.D. | 90.10 | 9.10 |
| PC conversion | 1.72 | 0.06 | 90.40 | 9.54 |

The invention claimed is:

1. A process for preparing Gadoteridol of formula (I):

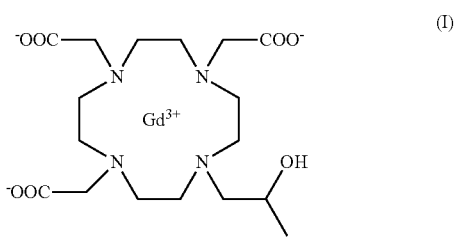

comprising the steps:

i) preparing propylene oxide by decomposition of propylene carbonate of formula:

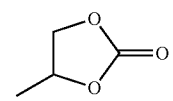

in the presence of an alkaline or alkaline earth metal halide as catalyst and directly reacting propylene oxide of formula:

with the compound of formula (II) without being isolated:

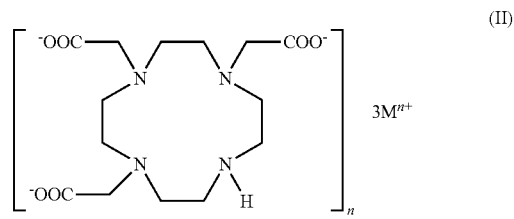

wherein M is an alkaline or alkaline earth metal and n is 1 or 2;

to obtain the compound of formula (III):

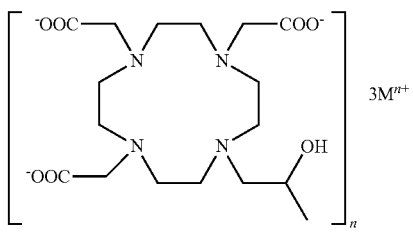

wherein M and n are as defined above;
ii) complexing the obtained compound of formula (III) with $Gd^{3+}$ metal ion to obtain Gadoteridol of formula (I).

2. The process according to claim 1 wherein the metal halide is selected from sodium, potassium or lithium iodide or bromide.

3. The process according to claim 2 wherein the metal halide is selected from sodium, potassium and lithium iodide.

4. The process according to claim 3 wherein the alkaline metal halides is sodium or lithium iodide.

5. The process according to claim 1 wherein the amount of the catalyst ranges from 0.1 to 100% w/w of the amount of propylene carbonate.

6. The process according to claim 5 wherein the amount of the catalyst ranges from 0.1 to 5% w/w of the amount of propylene carbonate.

7. The process according to claim 1 wherein propylene carbonate is heated at a temperature ranging from 160° C. to 250° C.

8. The process according to claim 1 wherein the compound of formula (II) is dissolved in water.

9. The process according to claim 1 wherein propylene carbonate is added in one portion, or in a semi-batch or continuous mode in a first reactor wherein it is heated in the presence of an alkaline or alkaline earth metal halide as catalyst and the forming propylene oxide is directly fed to a reactor containing compound (II).

10. The process according to claim 1 wherein M is an alkaline metal.

11. The process according to claim 1 wherein M is Na.

* * * * *